United States Patent
Ogata et al.

(10) Patent No.: US 7,632,486 B1
(45) Date of Patent: Dec. 15, 2009

(54) METHOD FOR DIAGNOSING BONE METASTASIS OF MALIGNANT TUMOR

(75) Inventors: Etsuro Ogata, c/o Cancer Institute Hospital of 1-37-1, Kami Ikebukuro, Toshima-Ku, Tokyo 170-455 (JP); Mitsuru Koizumi, Tokyo (JP); Shunji Takahashi, Tokyo (JP)

(73) Assignee: Etsuro Ogata, Tokyo (JP)

( * ) Notice: Subject to any disclaimer, the term of this patent is extended or adjusted under 35 U.S.C. 154(b) by 0 days.

(21) Appl. No.: 09/763,370

(22) PCT Filed: Aug. 20, 1999

(86) PCT No.: PCT/JP99/04480

§ 371 (c)(1), (2), (4) Date: Feb. 21, 2001

(87) PCT Pub. No.: WO00/11480

PCT Pub. Date: Mar. 2, 2000

(30) Foreign Application Priority Data

Aug. 21, 1998 (JP) ................................. 10-236146

(51) Int. Cl.
- A61K 49/00 (2006.01)
- C12Q 1/00 (2006.01)
- G01N 31/00 (2006.01)
- G01N 1/00 (2006.01)
- A01N 61/00 (2006.01)

(52) U.S. Cl. .............................. 424/9.2; 424/9.1; 435/4; 436/8; 436/174; 514/1; 514/2

(58) Field of Classification Search .................. 424/9.1, 424/9.2; 435/4; 514/1, 2; 436/8, 174
See application file for complete search history.

(56) References Cited

OTHER PUBLICATIONS

Plebani et al. New and Traditional Serum Markers of Bone Metabolism in the Detection of Skeletal Metastases. Biochemistry 29(1):67-72, Feb. 1996.*
Warrell. Gallium nitrate for the treatment of bone metastases. Cancer 80(8 Supplement): 1680-1685, 1997.*
Martinetti et al. Serum Markers of bone metastases in postmenopausal breast cancer patients treated with formestane. Tumor Biol. 18: 197-205, 1997.*
Koizumi et al. Bone metabolic markers in bone metastases. J Cancer Res Clin. Oncol. 121: 542-548, 1995.*
Koizumi et al. Bone metabolic markers in bone metastasis of breast cancer. Int. J. Clin. Oncol. 4: 331-337, 1999.*
Nakayama et al. Differences in Bone and Vitamin D Metabolism between Primary Hyperparathyroidism and Malignancy-Associated Hypercalcemia. Journal of Clinical Endocrinology and Metabolism 81(2): 607-611, 1996.*
Tähtelä R and Thölix E. Serum concentrations of type I collagen carboxyterminal telopeptide (ICTP) and type I procollagen carboxy- and aminoterminal propeptides (PICP, PINP) as markers of metastatic bone disease in breast cancer. Anticancer Res. Jul.-Aug., 1996;16(4B):2289-93. Abstract only.*
Akimoto S et al. Clinical usefulness of serum carboxyterminal propeptide of type I procollagen and pyridinoline cross-linked carboxyterminal telopeptide of type I collagen in patients with prostate cancer. Jpn J Clin Oncol. 26(3):157-63, Jun. 1996.*
M. Koizumi, "Bone Metastasis of Cancer and Osteal Metabolism Marker"; *Clinical Calcium*, vol. 8, No. 4, May 1998; pp. 98-100, Only Abstract in English.
S. Takahashi et al.; "Significance of Osteal Metabolism Marker for Diagnosing Bone Metastasis"; *Biotherapy*, vol. 11, No. 1, pp. 75-80, 1997, Only Abstract in English.
K. Nakaba; "Correlation Among the Measurement of Therapeutic Effects on Bone Metastasis foci, Osteal Metabolism Marker and the Condition of Bone Metastasis"; *Therapeutic Research*, vol. 16, No. 12, pp. 212-217, 1995, Only Abstract in English.
Mitsuru Koizumi et al, "Bone Metabolic Markers in Bone Metastases", J. Cancer Res. Clin. Oncol., V. 121, pp. 542-548, 1995.
Gary Stein et al, "Relationship of Cell Growth to the Regulation of Tissue-specific Gene Expression During Osteoblast Differentiation" The FASEB Journal, V. 4, pp. 3111-3123, Oct. 1990.
Patricia Ducy et al, "Increased Bone Formation in Osteocalcin-deficient Mice" Nature, V. 382; pp. 448-452, Aug. 1996.
Mona Calvo et al, "Molecular Basis and Clinical Application of Biological Markers of Bone Turnover", Endocrine Reviews, v. 17, N. 4, pp. 333-368, 1996.
Mitsuru Koizumi and Etsuro Ogata, "Bone Metabolic Markers in Bone Metastasis", The Bone, V. 10, N. 3, pp. 111-118, 1996.
M. Koizumi and E. Ogata, "Bone Metabolic Markers in Metastatic Bone Tumors" The Cancer Journal, vO1 11, N. 3, pp. 137-140, May-Jun. 1998.

* cited by examiner

*Primary Examiner*—Alana M Harris
(74) *Attorney, Agent, or Firm*—Browdy and Neimark, PLLC

(57) ABSTRACT

Bone metastasis and the efficacy of drugs in the treatment of malignant tumors such as breast cancer, prostatic cancer and lung cancer that cause the bone metastasis are diagnosed using a marker that reflects the activity of osteoblasts and a marker that reflects the action of osteoclasts.

21 Claims, 4 Drawing Sheets

METHOD FOR DIAGNOSING BONE METASTASIS OF MALIGNANT TUMOR

REFERENCE TO RELATED APPLICATIONS

The present application is the national stage under 35 U.S.C. §371 of international application PCT/JP99/04480, filed Aug. 20, 1999, which designated the United States, and was not published in English.

TECHNICAL FIELD

This invention relates to a method of diagnosing bone metastasis accompanying malignant tumors such as breast cancer, prostatic cancer and lung cancer; the invention also relates to a method of evaluating the therapeutic effect of drugs used to treat these diseases.

BACKGROUND ART

Bone metastasis of cancer is conventionally diagnosed by examining clinical symptoms of the patient or images taken by simple radiography, bone scintigraphy, CT, MRI, etc. From a visual viewpoint, bone metastases are classified as a dissolution type, a hardening type or a mixed type depending on the balance between bone dissolution and formation at the site of bone metastasis. While image diagnoses are highly reliable and useful, they are generally too expensive to be used for screening and monitoring purposes.

With the recent advances in the study of bone metabolism, various markers have been developed as indices of bone metabolism. Markers of bone formation and resorption are separately listed in Table 1. Attempts are being made to diagnose bone metastases of cancers using those bone metabolic markers (Koizumi, M. et al., Bone Metabolic Markers in Bone Metastases, J. Cancer Res. and Clin. Oncol., 121:541-548, 1995).

TABLE 1

Markers of bone formation (1) Type I procollagen peptides proliferation
    C-terminal propeptide (PICP)
    N-terminal propeptide (PINP)
(2) Alkali phosphatases matrix formation
    total alkali phosphatase (ALP)
    bone alkali phosphatase (BALP)
(3) Osteocalcin (OC) mineralization
    C-terminal fragments
    intermediate portions
    intact Markers of bone resorption (1) pyridinium cross-links
    total urinary pyridinoline•deoxypyridinoline (HPLC method)
    free urinary deoxypyridinoline (fDPD)
(2) pyridinium crosslinked collagen peptide fragments
    serum C-terminal telopeptide (ICTP)
    urinary C-terminal telopeptide (CTx)
    urinary N-terminal telopeptide (NTx)
(3) Tartrate-resistant acid phosphatase (TRAP)
(4) Galactosyl hydroxylysine (GHYL)
(5) Hydroxyproline
(6) N-terminal osteocalcin Most of the bone metabolic markers have as their rationale the measurement of metabolic products that are released into blood and urine in the process of formation and absorption of type I collagen which accounts for 90% of the bone matrix. To be more specific, type I procollagen which is synthesized during bone formation releases C- and N-terminal propeptides when it is converted to type I collagen and these propeptides serve as markers of bone formation. In the process of bone resorption, the type I collagen in the bone matrix undergoes metabolism to be released into blood and urine; the measured blood and urine levels of the released type I collagen serve as markers of bone resorption.

Bone formation is known to consist of three major phases depending upon the stage of proliferation and differentiation of osteoblasts; the first phase is where oesteoblasts proliferate and the matrix forms, the second phase is for matrix maturation and the third phase is for calcification, and different markers are known to appear at different phases (Stein, G. S. et al.: Relationship of Cell Growth to the Regulation of Tissue-Specific Gene Expression during Osteoblast Differentiation, FASEB J., 4:3111-3123, 1990).

In the phase of osteoblast proliferation and matrix formation, type I collagen forms actively and C- and N-terminal propeptides appear in the blood. In the phase of matrix maturation, bone alkali phosphatase (BALP) is generated actively, causing BALP to be secreted into the blood. At the stage of calcification, osteocalcin (OC) appears. Bone formation is accelerated in OC-deficient mice, suggesting that OC works as a suppressant of bone formation (Ducy, P. et al.: Increased Bone Formation in Osteocalcin-Deficient Mice; Nature, 382: 448-452, 1996).

In the box of "Markers of bone formation" in Table 1, "(1) proliferation" corresponds to the phase of osteoblast proliferation and matrix formation, "(2) matrix formation" to the phase of matrix maturation, and "(3) mineralization" to the phase of calcification.

While there are various markers of bone formation, they frequently behave differently depending upon the state of the disease and it is important to realize specifically in which phase each marker appears.

There are also various markers of bone resorption and as with the markers of bone formation, metabolic products of type I collagen are currently drawing special attention. In type I collagen, collagen of a triple-stranded structure occurs crosslinked with pyridinoline and deoxypyridinoline, so when it is destroyed upon bone resorption, pyridinoline and deoxypyridinoline cross-links having various sizes of N- and C-terminal amino acids attached thereto are released into the blood.

The measurements of resorptive markers include that of cross-links alone (urinary pyridinoline and deoxypyridinoline that are measured as free entities), that of cross-links including C-terminal amino acids (CTx and ICTP), and that of cross-links including N-terminal amino acids (NTx). For generalized details about bone metabolic markers, see the review article by Calvo et al. (Calvo, M. S. et al., Molecular Basis and Clinical Application of Biological Markers of Bone Turnover, Endocrine Rev., 17:333-368, 1996).

In bone metastasis, markers of bone metabolism behave somewhat differently than in metabolic bone diseases such as osteoporosis. Among formative markers, increased PICP and BALP are observed in bone metastasis of prostatic cancer which is a typical example of bone hardening metastases but there is no significant increase in the level of osteocalcin which rises in osteoporosis and other metabolic bone diseases. The mechanism behind these phenomena is not presently known. In breast cancer which involves bone metastasis of a mixed type, the levels of formative markers increase but not as much as in prostatic cancer. In lung cancer which involves many cases of bone metastasis of a dissolution type, there are no significant increases in the levels of formative markers.

Among resorptive markers, ICTP differs from the other bone metabolic markers in that it does not change greatly after menopause but it has been found to increase in bone metastasis of cancer. From the viewpoint of detecting bone metastasis, ICTP may be considered a good marker that is insensitive to enhanced bone resorption in the post-menopausal stage. The levels of resorptive markers increase not only in bone metastasis of lung cancer which is mostly of a dissolution type but also in bone metastasis of breast cancer which is mostly of a mixed type, as well as in bone metastasis of prostatic cancer which is of a hardening type.

DISCLOSURE OF THE INVENTION

While the studies of bone metabolic markers have seen remarkable advances, comparisons of their advantages and limitations are presently far from being thorough and given many various markers of bone resorption and formation, one cannot tell for sure which markers are currently the best in diagnosis of bone metastasis.

In clinical diagnosis of bone metastasis, choice of a marker is entirely up to the discretion of each doctor and no technique has yet been established that allows for systematic monitoring of bone metastasis.

An object, therefore, of the present invention is to provide a tool capable of systematic monitoring of bone metastasis.

Under the circumstances, the present inventors conducted intensive studies with a view to developing a tool for systematic monitoring of bone metastasis and found that this object could be attained by combining a marker (formative marker) that reflects the activity of osteoblasts with a maker (resorptive marker) that reflects the action of osteoclasts. The present invention has been accomplished on the basis of this finding.

Thus, according to one aspect of the invention, there is provided a method of diagnosing bone metastasis of malignant tumors using a marker that reflects the activity of osteoblasts and a marker that reflects the action of osteoclasts.

According to another aspect of the invention, there is provided a method of evaluating the therapeutic effect of drugs using a marker that reflects the activity of osteoblasts and a marker that reflects the action of osteoclasts.

BEST MODE FOR CARRYING OUT THE INVENTION

We now describe the findings which were the basis for accomplishing the present invention.

Figure 1:
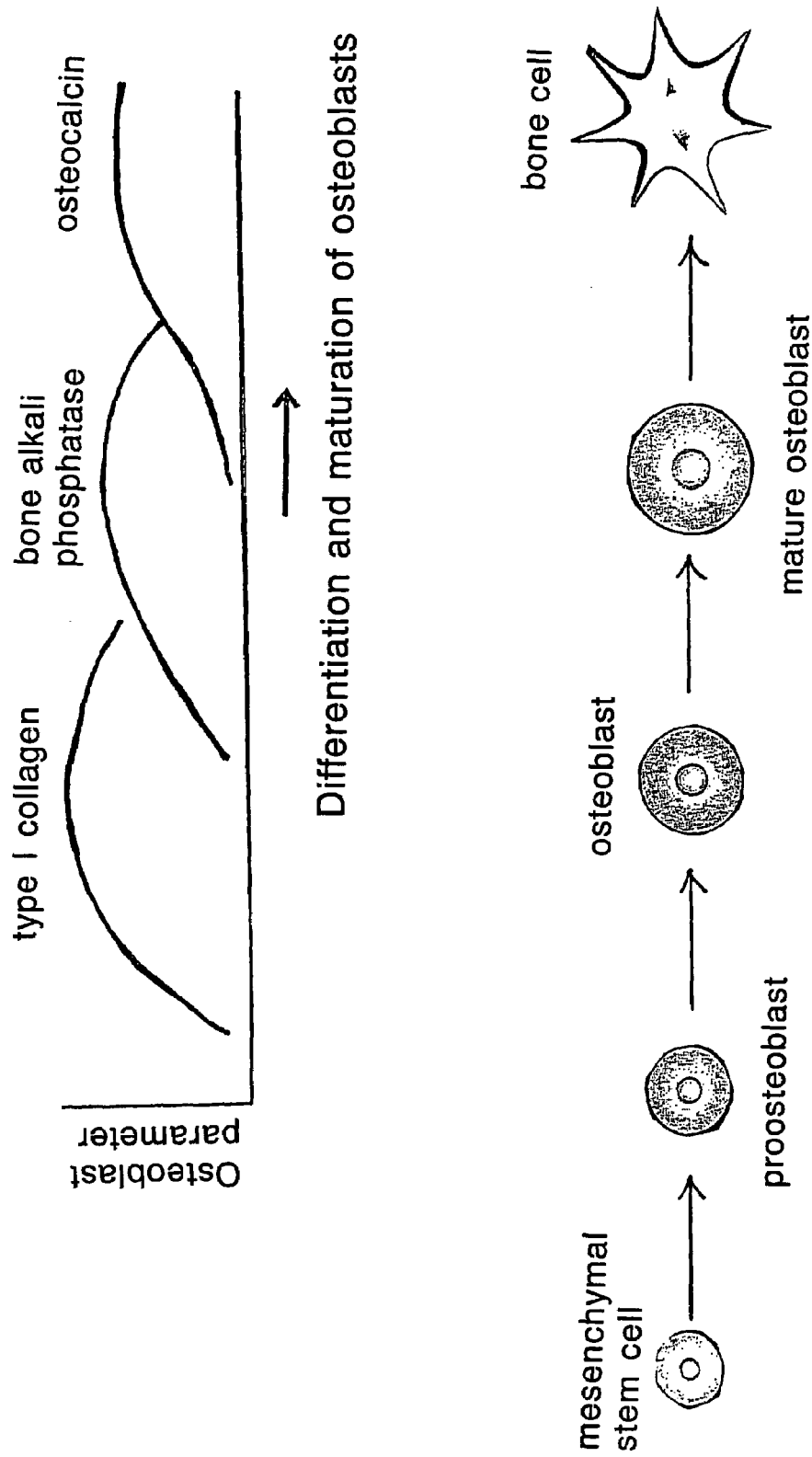
FIG. 1 is a diagram showing how three different markers begin to appear as osteoblasts differentiate.

(1) Markers of Bone Formation as Produced from Osteoblasts:

As FIG. 1 shows, the differentiation of osteoblasts involves shifts in marker expression from PICP and PINP (type I procollagen peptides) through BALP (bone alkali phophatase) to osteocalcin (Stein, G. S. et al., FASEB J., 4:3111-3123, 1990).

(2) Reactions of BALP and Osteocalcin to Chemotherapy in Patients with Prostatic Cancer and Breast Cancer Who were Suffering from Bone Metastasis:

The levels of two formative markers, BALP and osteocalcin, differed with the state of bone metastasis, as demonstrated in the following two Examples.

Example 1

During the period from October 1994 to April 1996, the levels of formative markers were measured in 43 prostatic cancer patients with bone metastasis and 46 prostatic cancer patients without bone metastasis. Of the 46 prostatic cancer patients who apparently had no bone metastasis, 29 had received prostatectomy or radiation therapy and the remaining 17 were newly diagnosed patients who received prostatectomy or radiation therapy after bone scintigraphy and serum sampling. The patients without bone metastasis were aged 69 on average (ranging from 47 to 85 years old). The progress of prostatic cancer in these patients was as follows: four patients at stage A, 14 at stage B, 19 at stage C, and 9 at stage D1. Of the 43 patients with bone metastasis, 9 were newly diagnosed and received hormone therapy after bone scintigraphy and serum sampling. The remaining 34 patients had received positive treatments by hormone therapy and/or chemotherapy at various time intervals from the start of these treatments. The patients with bone metastasis were aged 69 on average (ranging from 53 to 83 years old).

After obtaining informed consent from all patients, blood samples were taken during bone scintigraphy and sera were separated and stored frozen at −40° C. until analysis. Serum BALP was measured by enzyme immunoassay with an ALK-PHASE-B kit of Metra Biosystems. Serum osteocalcin was measured by immunoradiometric assay with a BGP-IRMA kit of Mitsubishi Chemical Corp.

Figure 2:
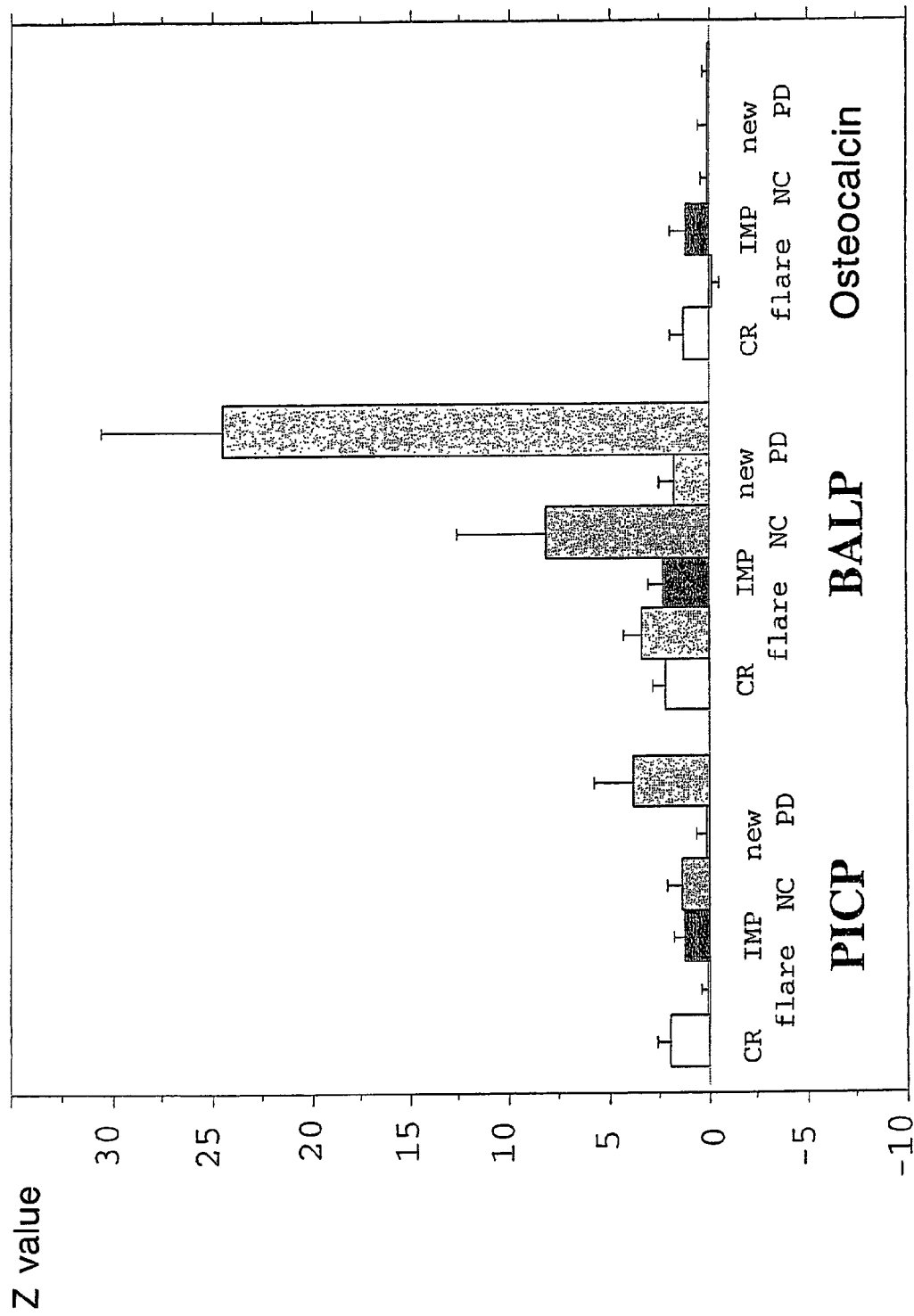
FIG. 2 is a graph showing the relationship between the efficacy of chemotherapy on patients with prostatic cancer involving bone metastasis and each of three markers, PICP, BALP and osteocalcin.

The results are shown in FIG. 2, in which Z value is defined by (measured value−average for the patients out bone metastasis)/(standard deviation of a patient without bone metastasis). In FIG. 2, CR, Flare, NC, IMP, new and PD have the following respective meanings.

| | |
|---|---|
| CR | complete remission |
| flare | flare-up [the treatment was effective but the bone metastasis appeared to have progressed on a bone scan (scintigraphic) image]. |
| NC | no change (no change was observed) |
| IMP | improvement (a sign of improvement was recognized). |
| New | diagnosed to have a new bone metastasis. |
| PD | progression of disease (the disease was found to have progressed). |

For each of these patient groups, BALP and osteocalcin had the following Z values.

| Z value of BALP | |
|---|---|
| CR | 2.18 |
| flare | 3.40 |
| NC | 8.23 |
| IMP | 2.39 |

-continued

|     |       |
| --- | ----- |
| new | 1.82  |
| PD  | 24.50 |

Z value of osteocalcin

|      |       |
| ---- | ----- |
| CR   | 1.30  |
| flare| −0.18 |
| NC   | 0.04  |
| IMP  | 1.25  |
| new  | 0.08  |
| PD   | 0.05  |

Using these values, a crossover index (Z osteocalcin/Z BALP) was calculated for each patients group.

Crossover index

|       |        |
| ----- | ------ |
| CR    | 0.596  |
| flare | −0.053 |
| NC    | 0.005  |
| IMP   | 0.523  |
| new   | 0.044  |
| PD    | 0.002  |

As is clear from the above data, BALP had a low Z value (2.18) in the CR group in which the treatments proved effective whereas it had a high Z value (24.50) in the PD group in which the disease worsened. On the other hand, osteocalcin had a high Z value (1.30) in the CR group but had a low Z value (0.05) in the PD group. The crossover index was 0.596 in the CR group but 0.002 in the PD group, with a marked difference being observed between the two groups. It can hence be concluded that the crossover index allows for both diagnosis of the progression of bone metastasis and evaluation of drug efficacy in the treatment of the disease.

Example 2

As in Example 1, the levels of formative markers (BALP and osteocalcin) were measured in a total of 850 patients with breast cancer, 644 of whom had bone metastasis and 206 having no bone metastasis. The patients with bone metastasis received chemotherapy or endocrine therapy targeted to the site of bone metastasis; they were classified into six groups, CR, NC, IMP, new and PD, according to the therapeutic efficacy achieved and the Z values of BALP and osteocalcin were determined in each group. On the basis of the measured Z values, a crossover index was calculated for each patient group.

After obtaining informed consent from all patients, blood samples were taken during bone scintigraphy and sera were separated and stored frozen at −40° C. until measurement. Serum BALP was measured by enzyme immunoassay with an ALKPHASE-B kit of Metra Biosystems. Serum osteocalcin was measured by immunoradiometric assay with a BGP-IRMA kit of Mitsubishi Chemical Corp. The results are shown below.

Z value of BALP

|     |       |
| --- | ----- |
| CR  | 0.741 |
| NC  | 1.514 |
| IMP | 0.735 |

-continued

|     |       |
| --- | ----- |
| new | 2.021 |
| PD  | 5.041 |

Z value of osteocalcin

|     |        |
| --- | ------ |
| CR  | 0.267  |
| NC  | 0.237  |
| IMP | 0.039  |
| new | −0.167 |
| PD  | 0.516  |

Crossover index

|     |        |
| --- | ------ |
| CR  | 0.360  |
| NC  | 0.157  |
| IMP | 0.053  |
| new | −0.083 |
| PD  | 0.102  |

Figure 3:
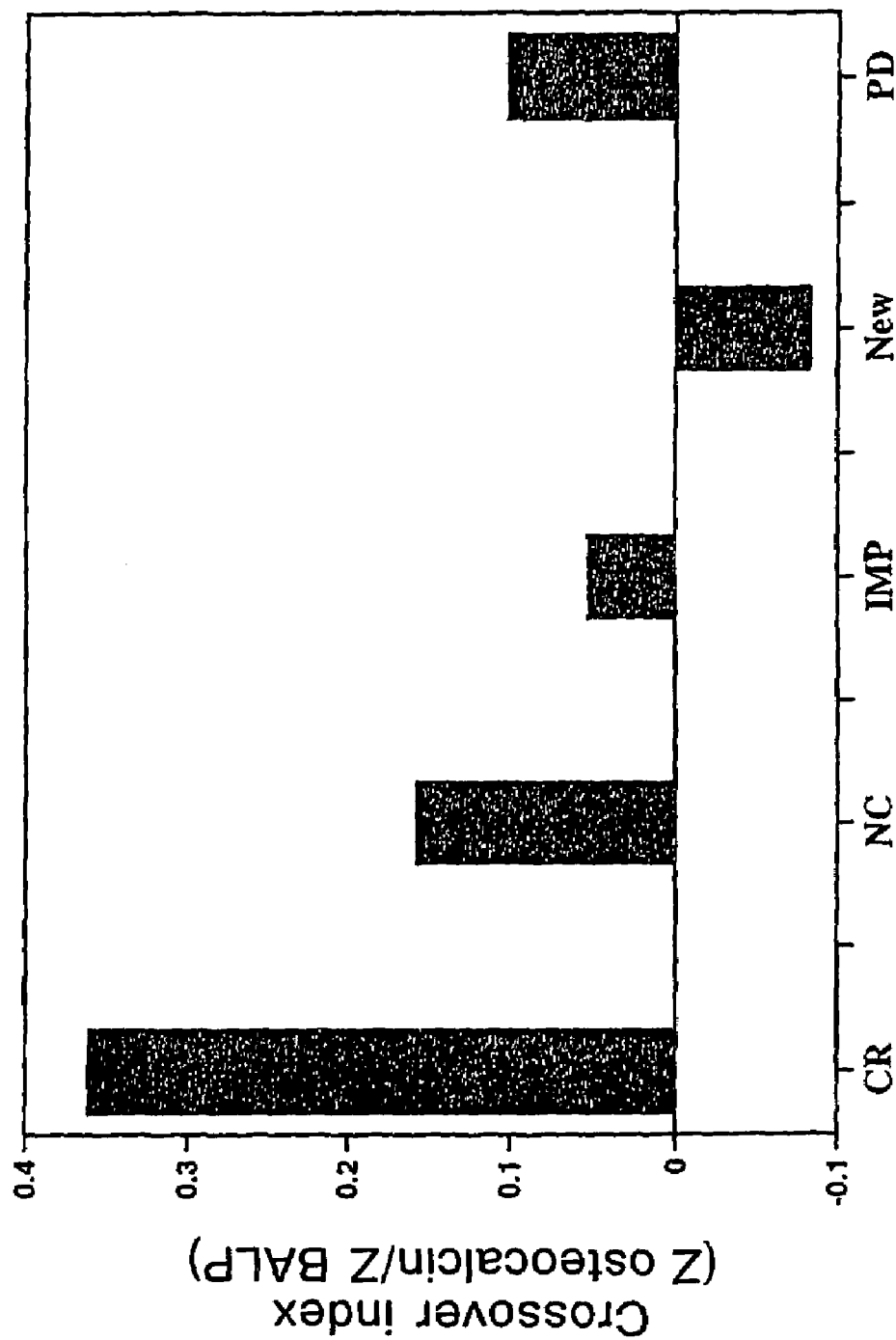
FIG. 3 is a graph showing the changes in a crossover index, osteocalcin/BALP, for patients with breast cancer.

FIG. 3 is a graph showing the changes in crossover index as observed in the respective groups CR, NC, IMP, new and PD. Obviously, the crossover index for the group CR in which the treatments proved effective was 0.360 whereas the value for the group PD in which the disease worsened was 0.102, with a marked difference being observed between the two groups. It can hence be concluded that as in the case of prostatic cancer, the crossover index allows for both diagnosis of the progression of bone metastasis of breast cancer and evaluation of drug efficacy in the treatment of the disease.

The results of Examples 1 and 2 showed that the patients with bone metastasis in group CR who were effectively treated by drugs had high crossover index values whereas the patients with bone metastasis in group PD who changed for the worse without any therapeutic effect had low crossover index values. It was therefore supported that a crossover index between two osteoblast markers was extremely effective in evaluating the degree of amelioration of bone metastasis (therapeutic efficacy of drugs).

In patients with prostatic cancer, the crossover index value of group CR was close to that of group IMP and so was the crossover index value of group NC to that of group PD; these data reflect the therapeutic efficacy for bone metastasis of prostatic cancer which was predominantly attributable to bone formation. The result from the patients with breast cancer was somewhat different in that the crossover index value of group NC was close to that of group PD whereas the crossover index value of group CR was not close to that of group IMP. The difference would have originated because breast cancer presents an image of bone metastasis to which bone dissolution is a more significant predisposing factor than bone formation. Therefore, in order to ensure that the progress of bone metastasis (the degree of aggravation) is diagnosed accurately, not only formative markers but also resorptive markers would have to be measured.

In Examples 1 and 2, the progress of bone metastasis of malignant tumors and the efficacy of their treatment by drugs were diagnosed by measuring the crossover index between osteocalcin which is a marker associated with the phase of calcification and BALP which is a marker associated with the phase of matrix maturation. The present inventors also verified that the progress of bone metastasis of malignant tumors and the efficacy of their treatment by drugs could be diagnosed by measuring the crossover index between osteocalcin which is a marker associated with the phase of calcification and PICP and PINP which are a marker associated with the phase of osteoblast proliferation and matrix formation. Needless to say, osteocalcin can be replaced by any other markers that are associated with the phase of calcification, PICP or PINP can be replaced by any other markers that are associated with the phase of osteoblast proliferation and matrix formation, and BALP can be replaced by any other markers that are associated with the phase of matrix maturation.

In the past, several markers of bone formation have been identified and their levels have been individually measured to show that different markers were produced at different times depending on the stage in differentiation and maturation of osteoblasts. However, it has not been shown clearly which of the formative markers should be exclusively used as indices of bone metastasis to reflect the fact that "differentiation and maturation of osteoblasts are suppressed by bone metastasis of cancer". It was entirely unexpected from the prior art that the progress of bone metastasis and the efficacy of its treatment by drugs could be evaluated by the above-defined crossover index.

The bone to which cancer has metastasized is broken down by osteoclasts. While several markers are known to be capable of evaluating the bone resorption that accompanies bone destruction, the degree of bone metastasis (worsening of the disease) and the effect of therapy in suppressing bone destruction can be evaluated definitely by identifying ICTP (type I collagen carboxy-terminal telopeptide) which is a collagen metabolite having a comparatively high molecular weight, validating ICTP as a reliable marker of bone resorption (see, for example, The Bone, Vol. 10, No. 3, pp. 111-118, 1996). Described below is an example showing the degree of bone metastasis and the effect of therapy in suppressing bone destruction.

Example 3

ICTP Level in Treatment of Breast Cancer

ICTP levels were measured in 23 patients with breast cancer who had received chemotherapy of bone metastasis by CAF regimen (C, cyclophosphamide; A, doxorubicin or Adriamycin; F, fluorouracil). The control group consisted of 9 patients with breast cancer who had no bone metastasis and received a CAF regimen as adjuvant therapy.

After obtaining informed consent from all patients, bone metabolic markers indicative of bone formation and resorption were measured. At the onset of CAF treatment and up to its end, blood samples were taken when bone scintigraphy was performed once a month and the sera were separated. The separated sera were stored frozen at −40° C. until analysis. A formative marker BALP was measured by enzyme immunoassay with an ALKPHASE-B kit of Metra Biosystems. A resorptive marker ICTP was measured by radioimmunoassay with Orion Diagnostica. The serum CA 15-3 was measured by immunoradiometric assay with Centocor. The measured values were expressed in terms of the average and SE (standard error). A test of significance was carried out by analysis of variance (ANOVA) according to the Bonferroni method.

Figure 4:
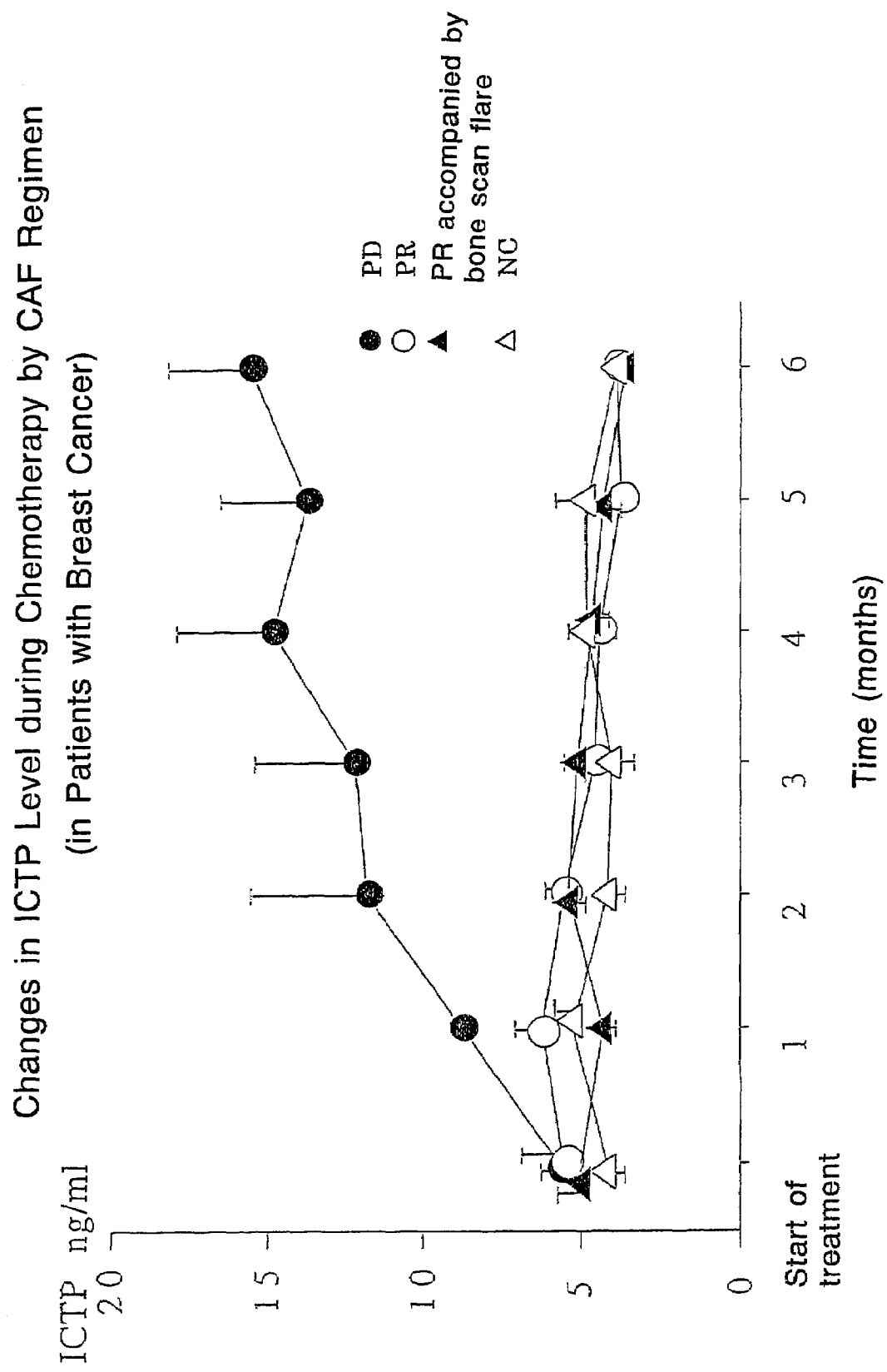
FIG. 4 is a graph showing the changes in the ICTP level during treatment of breast cancer.

The results are shown in FIG. 4, from which one can see that the ICTP values in the patients of group PD increased significantly over the ICTP values in the patients of group PR (partial response) and NC. The ICTP values of the patients of the "flare" group were significantly lower than those of the patients of group PD and substantially the same as those of the groups NC and PR without flare-up. The terms PD, flare and NC in FIG. 4 have the same meanings as in Example 1. PR means "partial therapeutic effect recognized".

No statistically significant difference was shown by the values of BALP and CA 15-3.

It is therefore concluded that by measuring the ICTP level, one can evaluate the degree of exacerbation of cancer metastasis to bone.

According to the findings in Examples 1-3, the amelioration of bone metastasis (therapeutic effect) and the degree of its exacerbation can be correctly diagnosed by monitoring two markers, one associated with osteoblasts and targeted to evaluation of therapeutic effect and the other associated with osteoclasts and targeted to evaluation of the worsening of the disease.

INDUSTRIAL APPLICABILITY

As described on the foregoing pages, the present invention provides a tool by which bone metastases caused by malignant tumors such as breast cancer, prostatic cancer and lung cancer and the therapeutic efficacy of drugs for the cancers causative of such metastases can be diagnosed much more accurately than by the prior art methods.

The invention claimed is:

1. A method of diagnosing amelioration and/or exacerbation of metastasis of malignant tumor to bone in a patient with a cancer disease,
   using markers for bone formation that reflect the activity of osteoblasts and markers that reflect the activity of osteoclasts,
   1) wherein the markers that reflect the activity of osteoblasts are
      a) a marker associated with the phase of calcification, and
      b) a marker associated with the phase of osteoblasts proliferation and/or matrix formation,
   2) wherein the marker that reflects the activity of osteoclasts is a marker associated with osteoclasts targeted to evaluation of worsening of the disease,
   whereby the amelioration of bone metastasis or therapeutic effect and the degree of the exacerbation of bone metastasis are diagnosed correctly by monitoring said two markers, one associated with osteoblasts and targeted to evaluation of therapeutic effect, and the other associated with osteoclasts and targeted to evaluation of worsening of the disease.

2. The method of claim 1, wherein the marker that reflects the activity of osteoblasts is:
   (1) a marker associated with the phase of osteoblasts proliferation and matrix formation and a marker associated with the phase of calcification; or
   (2) a marker associated with the phase of matrix maturation and a marker associated with the phase of calcification.

3. The method according to claim 1, wherein the marker that reflects the activity of osteoblasts is:
   1) Carboxyterminal propeptide of type I procollagen or Amino terminal propeptide of type I procollagen and osteocalcin; or
   2) Bone specific alkaliphosphatase and osteocalcin.

4. The method according to claim 1, wherein the marker that reflects the activity of osteoclasts is a marker associated with bone type I collagen.

5. The method according to claim 1, wherein the marker that reflects the activity of osteoclasts is deoxypyridinoline and/or Carboxyterminal telopeptide of type I collagen.

6. In a method of evaluating the efficacy of drugs for treatment of a cancer disease,
   using a formative marker that reflects the activity of osteoblasts or a marker that reflects the activity of osteoclasts,
   1) wherein the markers that reflect the activity of osteoblasts are
      a) a marker associated with the phase of calcification, and
      b) a marker associated with the phase of osteoblasts proliferation and/or matrix formation, 2) wherein the marker that reflects the activity of osteoclasts is a marker associated with osteoclasts targeted to evaluation of worsening of the disease, whereby the amelioration of bone metastasis or therapeutic effect and the degree of the exacerbation of bone metastasis are diagnosed correctly by monitoring said two markers, one associated with osteoblasts and targeted to evaluation of therapeutic effect, and the other associated with osteoclasts and targeted to evaluation of worsening of the disease.

7. The method according to claim 6, wherein the drug evaluated is a cancer control therapeutic agent.

8. The method according to claim 6, wherein the drug evaluated is a bone resorption suppressant.

9. The method according to claim 6, wherein the drug evaluated is an endocrine therapeutic agent.

10. The method according to claim 6, wherein the marker that reflects the activity of osteoblasts is:
   (1) a marker associated with the phase of osteoblast proliferation and matrix formation and a marker associated with the phase of calcification; or
   (2) a marker associated with the phase of matrix maturation and a marker associated with the phase of calcification.

11. The method according to claim 6, wherein the marker that reflects the activity of osteoblasts is:
   (1) Carboxyterminal propeptide of type I procollagen or Amino terminal propeptide of type I procollagen and osteocalcin; or
   (2) Bone specific alkaliphosphatase and osteocalcin.

12. The method according to claim 6, wherein the marker that reflects the activity of osteoclasts is a marker associated with bone type I collagen.

13. The method according to claim 6, wherein the marker that reflects the activity of osteoclasts is deoxypyridinoline and/or Carboxyterminal telopeptide of type I collagen.

14. The method according to claim 1 or 6, wherein said cancer disease is prostate cancer.

15. The method according to claim 1 or 6, wherein said cancer disease is breast cancer.

16. The method according to claim 6, wherein the drug evaluated is a cancer control therapeutic agent.

17. The method according to claim 6, wherein the drug evaluated is a bone resorption suppressant.

18. The method according to claim 6, wherein the drug evaluated is an endocrine therapeutic agent.

19. A method of evaluating the efficacy of a drug for the treatment of cancer or for the inhibition or amelioration of a metastasis of said cancer to bone in a patient with cancer, wherein said cancer is selected from the group consisting of prostate cancer and breast cancer,
   which comprises measuring for both (1) osteocalcin and (2) one marker selected from the group consisting of BALP, PICP and PINP,
   determining a Z value for each of said osteocalcin and said BALP, PICP or PINP, each said Z value being determined by dividing the difference between said measured value for said patient and an average value for patients without bone metastasis, by a standard deviation of a patient without bone metastasis, and determining a crossover index by dividing said Z value for osteocalcin by said Z value for BALP, PICP or PINP,
   said crossover index providing a diagnosis of progression of bone metastasis and evaluation of drug efficacy in the treatment of said patient for said cancer;
   wherein assessing or judging amelioration and/or exacerbation of metastasis with regard to the Z value is carried out in comparison with data for CR, PD, IMP and/or NC.

20. A method of diagnosing amelioration and/or exacerbation of metastasis of malignant tumor to bone in a patient with breast cancer,
   using markers that reflect the activity of osteoblasts and markers that reflect the activity of osteoclasts,
   1) wherein the markers that reflect the activity of osteoblasts are
      (a) a marker associated with the phase of calcification, and
      (b) a marker associated with the phase of osteoblasts proliferation and/or matrix formation,
   2) wherein the marker that reflects the activity of osteoclasts is a marker associated with osteoclasts targeted to evaluation of worsening of the disease,
   comprising testing blood from said patient for a marker of bone metabolism,
   wherein the amelioration of bone metastasis or therapeutic effect and the degree of the exacerbation of bone metastasis are diagnosed by monitoring said markers, and
   said testing comprising measuring for both osteocalcin and BALP,
   determining a Z value for each of said BALP and osteocalcin, each said Z value being determined by dividing the difference between said measured value for said patient and an average value for patients without bone metastasis, by a standard deviation of a patient without bone metastasis, and
   determining a crossover index by dividing said Z value for osteocalcin by said Z value for BALP,
   said crossover index providing a diagnosis of progression of bone metastasis in the treatment of said patient for breast cancer.

21. A method of evaluating the efficacy of drugs for treatment of breast cancer,
   using a formative marker that reflects the activity of osteoblasts and a marker that reflects the activity of osteoclasts,
   1) wherein the markers that reflect the activity of osteoblasts are
      (a) a marker associated with the phase of calcification, and
      (b) a marker associated with the phase of osteoblasts proliferation and/or matrix formation,
   2) wherein the marker that reflects the activity of osteoclasts is a marker associated with osteoclasts targeted to evaluation of worsening of the disease,
   comprising testing blood from said patient for a marker of bone metabolism,
   wherein the amelioration of bone metastasis or therapeutic effect and the degree of the exacerbation of bone metastasis are diagnosed correctly by monitoring said markers, and
   said testing comprises measuring for both osteocalcin and BALP,
   determining a Z value for each of said osteocalcin and said BALP, each said Z value being determined by dividing the difference between said measured value for said patient and an average value for patients without bone metastasis, by a standard deviation of a patient without bone metastasis, and determining a crossover index by dividing said Z value for osteocalcin by said Z value for BALP, said crossover index providing a diagnosis of progression of bone metastasis and evaluation of drug efficacy in the treatment of said patient for said cancer; wherein a higher index indicates amelioration of the patient's condition.

* * * * *